United States Patent [19]
Kelley et al.

[11] Patent Number: 5,585,534
[45] Date of Patent: Dec. 17, 1996

[54] INBRED CORN LINE DESIGNATED ZS0853

[75] Inventors: Scott N. Kelley, Doniphan, Nebr.; Mark J. Messmer, Ankeny, Iowa

[73] Assignee: Zeneca Limited, London, England

[21] Appl. No.: 200,193

[22] Filed: Feb. 22, 1994

[51] Int. Cl.⁶ .............................. A01H 1/02; A01H 4/00; A01H 5/00; C12N 5/04
[52] U.S. Cl. ................ 800/200; 800/250; 800/DIG. 56; 435/240.4; 435/240.49; 435/240.5; 47/58; 47/DIG. 1
[58] Field of Search ..................................... 800/200, 205, 800/235, 250, DIG. 56; 435/240.1, 240.4, 240.47, 240.49, 240.5; 47/58.01, 58.03, 58, DIG. 1

[56] References Cited

U.S. PATENT DOCUMENTS 5,059,745  10/1991  Foley ...................................... 800/200

OTHER PUBLICATIONS

Green et al. 1982. In Maize for Biological Research Sheridan, ed. pp. 367–372.

MBS® Incorporated. 1993. Genetics Handbook. 20th Edition. pp. 16–17.

Forsberg, R. A., R. R. Smith. Sources, Maintenance, and Utilization of Parental Material, pp. 65–81. Hybridation of Crop Plants. ASA–CSSA, Madison, Wisconsin. 1980.

Hallauer, A. R., Wilbert A. Russell, and K. R. Lamkey. Corn Breeding, pp. 463–564. Corn and Corn Improvement. ASA–CSSA–SSSA, Madison, Wisconsin. 1988.

Meghji, M. R., J. W. Dudley, R. J. Lambert, and G. F. Sprague. Inbreeding Depression, Inbred and Hybrid Grain Yields, and Other Traits of Maize Genotypes Representing Three Eras, pp. 545–549. Crop Science, vol. 24, May–Jun. 1984.

Phillips, R. L., D. A. Somers, and K. A. Hibberd. Cell/Tissue Culture and In Vitro Manipulation, pp. 345–387. Corn and Corn Improvement. ASA–CSSA–SSSA, Madison, Wisconsin. 1988.

Wright, Harold. Commercial Hybrid Seed, pp. 161–176. Hybridization of Crop Plants. ASA–CSSA, Madison, Wisconsin. 1980.

Wych, Robert D. Production of Hybrid Seed Corn, pp. 565–607. Corn and Corn Improvement. ASA–CSSA–SSSA, Madison, Wisconsin. 1988.

*Primary Examiner*—Erich E. Veitenheimer
*Attorney, Agent, or Firm*—Dana Rewoldt

[57] ABSTRACT

An inbred corn line designated ZS0853, including plants of ZS0853 and pollen and seed of such plants. Also, a method of producing a corn plant by crossing ZS0853 either with itself or with another corn line and the first generation plants and seeds produced by such crosses.

11 Claims, No Drawings

INBRED CORN LINE DESIGNATED ZS0853

FIELD OF THE INVENTION

Generally the present invention relates to the field of plant breeding. In particular the present invention concerns the development of corn plants. More specifically, the present invention relates to the development of elite germplasm capable of forming high performance hybrids when crossed with another elite inbred.

BACKGROUND OF THE INVENTION

The invention relates generally to corn breeding and, more specifically, to an inbred corn line designated ZS0853. Corn or maize (*Zea mays L.*), is an agronomic crop of great commercial significance both in the United States and in many countries of the world. Corn is used as feed both for animals and humans and has a wide variety of industrial applications. At the commercial production level, the dominant form of corn is single cross hybrids or varieties. Homozygous inbred lines, although not grown as a commercial crop, are extremely important as the source material for the production of hybrid varieties. The cross-pollination of two distinct homozygous inbred lines produces a first generation hybrid variety that is heterozygous at most gene loci.

The goal of plant breeding is to combine in a single variety/hybrid various desirable agronomic traits. For field crops, these traits may include resistance to diseases and insects, reducing the time to crop maturity, greater yield, and better agronomic quality.

Field crops are bred through techniques that take advantage of the plant's method of pollination. A plant is self-pollinated if pollen from one flower is transferred to the same or another flower of the same plant. A plant is cross-pollinated if the pollen comes from a flower on a different plant.

Plants that have been self-pollinated and selected for type for many generations become homozygous at almost all gene loci and produce a uniform population of true breeding progeny. A cross between two homozygous lines produce a uniform population of hybrid plants that may be heterozygous for many gene loci.

Corn plants (*Zea mays L.*) can be bred by both self-pollination and cross-pollination techniques. Corn has separate male and female flowers on the same plant, located on the tassel and the ear, respectively. Natural pollination occurs in corn when wind blows pollen from the tassels to the silks that protrude from the tops of the incipient ears.

The development of corn hybrids requires the development of homozygous inbred lines, the crossing of these lines to make hybrids and the evaluation of the resulting hybrids. Pedigree breeding and recurrent selection breeding methods are used to develop inbred lines from breeding populations. Breeding programs combine the genetic backgrounds from two or more inbred lines or various other broad-based sources into breeding pools from which new inbred lines are developed by successive generations of inbreeding and selection of desired phenotypes. The new inbreds are crossed with other existing inbred lines and the single cross hybrids from these crosses are evaluated extensively in field performance trials to determine which of those have agronomically desirable potential.

New inbred lines are developed by plant breeders through cross pollination of breeding materials having complementary desirable characteristics which results in a breeding population genetically segregating for a number of important agronomic traits. After initial development of this breeding population, breeders perform a number of successive generations of inbreeding and selection. The objective of these inbreeding and selection generations is to identify and genetically fix a new inbred line which has improved agronomic characteristics. These improved characteristics may be per se traits such as seed yield, seed quality, or disease resistance. However, the primary objective of most breeding programs is to identify new inbred lines which produce improved hybrid plant characteristics such as grain yield and harvestability when the new lines are crossed to other existing inbred lines to produce hybrids.

The process of determining whether newly developed inbred lines provide improved characteristics in hybrids produced using the new line involves extensive field evaluation and testing of the hybrid product. Each newly developed inbred line provides potentially much different contributions to hybrid combinations than its progenitors. Each inbred corn line also is true breeding. In layman's terms this means that when an inbred corn line is planted in isolation and allowed to pollinate itself, the resulting progeny will produce corn plants essentially genetically and phenotypically indistinguishable from the parent inbred.

A single cross hybrid corn variety is the cross of two true breeding inbred lines, each of which has a genetic composition which complements the other. They hybrid progeny of the first generation cross between two parent lines is designated "$F_1$". In the hybrid seed development process, the $F_1$ hybrid seed is that which is sold to and planted by commercial growers. The preferred $F_1$ hybrid seed source is that which produces the highest level of vigor, agronomic strength, and yield compared to other $F_1$ hybrid alternatives.

Because the parents of an $F_1$ hybrid are true breeding, the seed resulting from a cross between the two parents will all be genetically identical, and will thus yield a stable and predictable phenotype in the commercial grower's fields. Also, because these parents are true breeding, they can be individually reproduced continually by open pollination in an isolated environment. Thus, it follows that the $F_1$ hybrid can be continuously reproduced from the parent lines.

A single cross hybrid is produced when two inbred lines are crossed to produce the $F_1$ progeny. A double cross hybrid is produced from four inbred lines crossed in pairs (A×B and C×D) and then the two $F_1$ hybrids are crossed again (A×B)× (C×D). Much of the hybrid vigor exhibited by $F_1$ hybrids is lost in the next generation $F_2$. Consequently, seed from hybrid varieties is not used for planting stock.

Corn is an important and valuable field crop. Thus, a continuing goal of plant breeders is to develop high-yielding corn hybrids that are agronomically sound based on stable inbred lines. The reasons for this goal are obvious: to maximize the amount of grain produced with the inputs used and minimize susceptibility to environmental stresses. To accomplish this goal, the corn breeder must select and develop superior inbred parental lines for producing hybrids. This requires identification and selection of genetically unique individuals which in a segregating population occur as the result of a combination of genetic recombinations plus the independent assortment of specific combinations of alleles at many gene loci which results in specific genotypes. Based on the number of segregating genes, the frequency of occurrence of an individual with a specific genotype is less than 1 in 10,000. Thus even if the entire genotype of the parents has been characterized and the desired genotype is known, only a few if any individuals having the desired genotype may be found in a large segregating population. Typically, however, the genotype of neither the parents nor the desired genotype is known in any detail.

Because commercial corn production relies on the development of novel and improved inbred corn lines, considerable money and effort is devoted by commercial seed companies and plant breeders to the development of inbred lines with the combining ability to produce first generation hybrid corn with the characteristics of high yield, resistance to disease and pests, improved plant stability, uniform phenotypical characteristics to facilitate machine harvesting, and so on, all with the goal of maximizing the efficient use of land and other resources in the production of foodstuffs and raw agricultural materials.

SUMMARY OF THE INVENTION

An object of the present invention is to produce an inbred corn line that can be used to form an excellent hybrid for use in the Central Region of the U.S. corn belt.

Another object of the present invention is to provide an inbred that has a generally broad based combining ability with other full season inbreds to produce high yields in hybrid combination.

Still another object of the present invention is to produce an inbred that has excellent tolerance to common corn rust.

Broadly the present invention is an inbred corn line designated ZS0853 and the plant or plants or the pollen or seed or seeds. Additionally the invention includes inbred corn plants with the phenotypic, physiological and morphologic characteristics of inbred corn line designated ZS0853.

A method is also contemplated within the present invention. A method for producing a corn plant, comprising the step of using a first parent corn plant with a second parent corn plant wherein the first or second parent corn plant is the inbred corn plant having designation ZS0853. The method wherein the first and second parent corn plants are both from the inbred corn line designated ZS0853.

The invention also includes the first generation ($F_1$) hybrid corn plant produced by crossing a first inbred female corn plant with a second inbred male corn plant, wherein the first or second parent corn plant is the inbred corn plant having the designation ZS0853. The female corn plant can be detasselled, male-sterile, mutant corn line lacking tassels, chemically altered to deter tasseling and the like as known in the art. The male corn plant can be female-sterile, de-earred, a mutant corn lacking ears, chemically altered to deter formation of ears or simply a corn plant used to pollinate from which ears are not harvested and the like.

The hybrid corn plant wherein the inbred corn plant having the designation ZS0853 is the female parent. The hybrid corn plant wherein the inbred corn plant having the designation ZS0853 is the male parent. A method for producing first generation ($F_1$) hybrid corn seed, comprising the step of crossing a first inbred parent corn plant with a second inbred parent corn plant, wherein the first or second parent corn plant is the inbred corn plant having the designation ZS0853. A first generation ($F_1$) hybrid corn plant produced by growing the hybrid corn seed. A plant cell which, upon growth and differentiation, produces the plant designated ZS0853.

DETAILED DESCRIPTION OF THE INVENTION

DEFINITIONS

In the description and examples which follow, a number of terms are used. In order to provide a clear and consistent understanding of the specifications and claims, including the scope to be given such terms, the following definitions are provided.

BL MOIST

The moisture percentage of the grain at black layer, ie, when 50% of the plants per plot have reached physiological maturity.

COLD GERM

Cold Germ is a measurement of seed germination under cold soil conditions. Data is reported as percent of seed germinating.

EMERGE

The percent of emerged plants per plot (planted at the same seedling rate) collected when plants have two fully developed leaves.

GI

This is a selection index which provides a single quantitative measure of the worth of a hybrid based on four traits. Yield is the primary trait contributing to index values.

GLS

Grey Leaf Spot (*Cercospora Zeae*) disease rating. This is rated on a 1–9 scale with a "1" being very susceptible, and a "9" being very resistant.

GW

Goss' Wilt (*Corynebacterium nebraskense*). This is rated on a 1–9 scale with a "1" being very susceptible, and a "9" being very resistant.

HEATP10

The number of Growing Degree Units (GDU's) or heat units required for an inbred line or hybrid to have approximately 10 percent of the plants shedding pollen. This trait is measured from the time of planting. Growing Degree Units are calculated by the Barger Method where the GDU's for a 24 hour period are:

$$GDU = \left( \frac{\text{Max Temp (°F.)} - \text{Min Temp (°F.)}}{2} \right) - 50$$

The highest maximum temperature used is 86° F. and the lowest minimum temperature used is 50° F. For each inbred or hybrid it takes a certain number of GDU's to reach various stages of plant development.

HEATBL

The number of GDU's after planting when approximately 50 percent of the inbred or hybrid plants in a plot have grain which has reached physiological maturity (black layer).

HEATPEEK

The number of GDU's after planting of an inbred when approximately 50 percent of the plants show visible tassel extension.

HEATP50

The number of GDU's required for an inbred or hybrid to have approximately 50 percent of the plants shedding pollen. Growing Degree Units are calculated by the Barger Method as shown in the HEATP10 definition.

HEATP90

The number of GDU's accumulated from planting when the last 10 percent of plants in an inbred or hybrid are still shedding enough viable pollen for pollination to occur. Growing Degree Units are calculated by the Barger Method as shown in the HEATP10 definition.

HEATS10

The number of GDU's required for an inbred or hybrid to have approximately 10 percent of the plants with silk emergence of at least 0.5 inches. Growing Degree Units are calculated by the Barger Method as shown in the HEATP10 definition.

HEATS50

The number of GDU's required for an inbred or hybrid to have approximately 50 percent of the plants with silk emergence of at least 0.5 inches. Growing Degree Units are calculated by the Barger Method as shown in the HEATP10 definition.

HEATS90

The number of GDU's required for an inbred or hybrid to have approximately 90 percent of the plants with silk emergence of at least 0.5 inches. Growing Degree Units are calculated by the Barger Method as shown in the HEATP10 definition.

$MDMV_A$

Maize Dwarf Mosaic Virus strain A. The corn is rated on a 1–9 scale with a "1" being very susceptible, and a "9" being very resistant.*

*Resistance on a scale of 1–9 with 9 evidencing the trait most strongly: 1–2.9 ratings are susceptible, 3–5.9 ratings are intermediate, and 6–9 ratings are resistant.

$MDMV_B$

Maize Dwarf Mosaic Virus strain B. This is rated on a 1–9 scale with a "1" being very susceptible and a "9" being very resistant.*

*Resistance on a scale of 1–9 with 9 evidencing the trait most strongly: 1–2.9 ratings are susceptible, 3–5.9 ratings are intermediate, and 6–9 ratings are resistant.

MOISTURE

The average percentage grain moisture of an inbred or hybrid at harvest time.

NLB

Northern Leaf Blight (*Exserohilum turcicum*) disease rating. This is rated on a 1–9 scale with a "1" being very susceptible, and a "9" being very resistant.*

*Resistance on a scale of 1–9 with 9 evidencing the trait most strongly: 1–2.9 ratings are susceptible, 3–5.9 ratings are intermediate, and 6–9 ratings are resistant.

PCT TILLER

Percentage of plants in a plot which have tillers.

PLANT HEIGHT

The distance in centimeters from ground level to the base of the tassel peduncle.

RM

Predicted relative maturity based on the moisture percentage of the grain at harvest. This rating is based on known set of checks and utilizes standard linear regression analyses and is referred to as the Minnesota Relative Maturity Rating System.

SHED

The volume of pollen shed by the male flower rated on a 1–9 scale where a "1" is a very light pollen shedder, a "4.5" is a moderate shedder, and a "9" is a very heavy shedder.

SLB

Southern Leaf Blight (*Bipolaris maydis*) disease rating. This is rated on a 1–9 scale with a "1" being very susceptible, and a "9" being very resistant.*

*Resistance on a scale of 1–9 with 9 evidencing the trait most strongly: 1–2.9 ratings are susceptible, 3–5.9 ratings are intermediate, and 6–9 ratings are resistant.

TWT

The measure of the weight of grain in pounds for a one bushel volume adjusted for percent grain moisture.

VIGOR

Visual rating of 1 to 9 made 2–3 weeks post-emergence where a "1" indicates very poor early plant development, and a "9" indicates superior plant development.

WARM GERM

A measurement of seed germination under ideal (warm, moist) conditions. Data is reported as percent of seeds germinating.

YIELD

Actual yield of grain at harvest adjusted to 15.5% moisture. Measurements are reported in bushels per acre.

% DROPPED EARS

Percentage of plants in a plot which dropped their primary ear divided by the total number of plants per plot.

% LRG FLAT

Percentage by weight of shelled corn that passes through a 26/64 inch round screen and a 14/64 inch slot screen, but does not pass through a screen with 205/64 inch round openings.

% LRG ROUND

Percentage by weight of shelled corn that passes through a 26/64 inch round screen, but does not pass through a 14/64 inch slot screen or a screen with 205/64 inch round openings.

% MED FLAT

Percentage by weight of shelled corn that passes through a 20/64 inch round screen and a 13/64 inch slotted screen, but does not pass through a screen with 17/64 inch round openings.

% MED ROUND

Percentage by weight of shelled corn that passes through a 20/64 inch round screen, but does not pass through a 13/64 inch slot screen or a screen with 17/64 inch round openings.

% SML FLAT

Percentage by weight of shelled corn that passes through a 17/64 inch round screen and a 12/64 inch slotted screen, but does not pass through a screen with 15/64 inch round openings.

% SML ROUND

Percentage by weight of shelled corn that passes through a 17/64 inch round screen, but does not pass through a 12/64 inch slotted screen or a screen with 15/64 inch round openings.

% ROOT LODGE

Number of plants in a plot leaning more that 30 degrees from vertical divided by total plants per plot.

% STALK LODGE

Number of plants in a plot with the stalk broken below the primary ear node divided by the total plants per plot.

The yellow dent corn inbred line ZS0853 has unique and superior characteristics. Inbred corn line ZS0853 has proven to be acceptable as a female and acceptable as a male line in producing $F_1$ hybrids. ZS0853 is acceptable for use as a male parent because of its pollen shed rating which overall environments is 7 on a scale of 0=sterile and 9=heavy shedder. Inbred line ZS0853 is adapted for use in the Central regions of the United States and in other regions of the world having similar environmental characteristics. This inbred can be used to produce hybrids from approximately 105–115 relative maturity based on the Minnesota Relative Maturing Rating System for harvest moisture of grain. ZS0853 is unique as a female parent because it shows specific combining ability with a variety of full season males. This inbred is characterized by excellent resistance levels to many plant diseases including common corn rust. As a female, ZS0853 is characterized by exhibiting excellent resistance to common corn rust, Goss' Wilt, and $MDMV_A$.

The inbred has shown uniformity and stability within the limits of environmental influence for all the traits as described in the Variety Descriptors (Table 1) that follows. Most of the data in the Variety Descriptors were collected at Slater, Iowa. Numeric data was generated from means over all environments where the inbred was evaluated.

The inbred has been self-pollinated for approximately 6–8 generations. During plant selection in each generation the uniformity of plant type was selected to ensure homozygosity and phenotypic stability. The line has been increased in isolated farmland environments with data on uniformity and agromonic traits being observed to assure uniformity and stability. No variant traits have been observed or are expected in ZS0853.

The best method of producing the invention, ZS0853 which is substantially homozygous, is by planting the seed of ZS0853 which is substantially homozygous and self-pollinating or pollinating the resultant plant in an isolated environment, and harvesting the resultant seed or the resultant pollen.

TABLE 1

ZS0853
VARIETY DESCRIPTION INFORMATION
1. Type: Dent
2. Region Best Adapted: Central
INBRED

```
#3          MATURITY
DAYS        HEAT UNITS
               1551.5 FROM EMERGENCE TO 50% OF PLANTS IN SILK
               1551.5 FROM EMERGENCE TO 50% OF PLANTS IN POLLEN
                  FROM 10% TO 90% POLLEN SHED
#4          PLANT
DATA        4 ANTHOCYANIN OF BRACE ROOTS: I=ABSENT 2=FAINT 3=MODERATE 4=DARK
#5          LEAF
COLOR/DATA
               3 LEAF COLOR *MUNSELL CODE - 5GY 314
               7 LEAF SHEATH PUBESCENCE (I=NONE TO 9=PEACH FUZZ)
               8 MARGINAL WAVES (1 =NONE TO 9=MANY)
               4 LONGITUDINAL CREASES (I =NONE TO 9=MANY)
#6          TASSEL
COLOR/DATA
               7 POLLEN SHED (0=STERILE TO 9=HEAVY SHEDDER)
               11 ANTHER COLOR *MUNSELL CODE - 5R 5/6
               1 GLUME COLOR   *MUNSELL CODE - 5GY 6/8
               2 BAR GLUME 1=ABSENT 2=PRESENT
#7A         EAR (UNHUSKED DATA)
17 AND 5 SILK COLOR (3 DAYS AFTER EMERGE.)*MUNSELL CODE - 5R 416 AND 2.5GY 8/8
               2 FRESH HUSK CO. (25 DAYS AFTER 50% SILK)*MUNSELL CODE - SGY 6/8
               22 DRY HUSK COLOR(65 DAYS AFTER 50% SILK)*MUNSELL CODE - 2.5Y 8/6
               1 POSITION OF EAR AT DRY HUSK 1=UPRIGHT 2=HORIZONTAL 3=PENDENT
               7 HUSK TIGHTNESS (1=VERY LOOSE TO 9=VERY TIGHT)
               2 HUSK EXTENSION AT HARVEST(1=EXPOSED EAR 2=8CM 3=8–10CM 4=>10CM)
#7B         EAR (HUSKED DATA)
```

TABLE 1-continued

ZS0853
VARIETY DESCRIPTION INFORMATION
1. Type: Dent
2. Region Best Adapted: Central
INBRED

|  |  |
|---|---|
|  | 2 KERNEL ROWS: 1=INDISTINCT 2=DISTINCT |
|  | 2 ROW ALIGNMENT:1=STRAIT 2=SLIGHT CURVE 3=SPIRAL |
|  | 2 EAR TAP ER: 1=STRAIT 2=AVERAGE 3=EXTREME |
| #8 | KERNEL(DRY) |
| COLORIDATA | **SOME CROWNS ARE LIGHTER AND COVER A LARGER AREA OF THE SEED. |
| **2 | ALEURONE COLOR PATTERN: 1=HOMO. 2=SEG. |
|  | 7 ALEURONE COLOR *MUNSELL CODE - 2.5Y 7/10 |
|  | 21 HARD ENDOSPERM COLOR*MUNSELL CODE - 2.5Y 7/10 |
|  | 7 CROWN COLOR *MUNSELL CODE - 2.5Y 8/10 |
| #9 | COB |
|  | 11 COB COLOR *MUNSELL CODE - 5R 7/8 |

COLOR CHOICES (Use in conjunction with Munsell color code to describe all color choices
01=Light Green
02=Medium Green
03=Dar Green
04=Very Dark Green
05=Green-Yellow
06=Pale Yellow
07=Yellow
08=Yellow-Orange
09=Salmon
10=Pink-Orange
11=Pink
12=Light Red
13=Cherry Red
14=Red
15=Red & White
16=Pale Purple
17=Purple
18=Colorless
19=White
20=White Capped
21=Buff
22=Tan
23=Brown
24=Bronze
25=Variegated (Describe)
26=Other (Describe)

1993 PRODUCTION TECHNOLOGY PVP TRAITS
INBRED

|  |  | N | MEAN |
|---|---|---|---|
| #10 | EAR HEIGHT(CM) | 15 | 65.73 |
|  | LENGTH OF PRIMARY EAR LEAF(CM) | 15 | 14.80 |
|  | WIDTH OF PRIMARY EAR LEAF(CM) | 15 | 9.07 |
|  | TOP EAR INTERNODE(CM) | 15 | 12.87 |
|  | DEGREE OF LEAF ANGLE | 15 | 60.73 |
|  | # OF EARS PER PLANT | 15 | 1.67 |
|  | # OF LEAVES ABOVE TOP EAR | 15 | 5.20 |
|  | # OF PRIMARY LATERAL TASSEL BRANCHES | 15 | 5.00 |
|  | PLANT HEIGHT(CM) | 15 | 195.9 |
|  | TASSEL LENGTH(CM) | 15 | 43.80 |
|  | TASSEL BRANCH ANGLE | 15 | 33.93 |
|  | # OF TILLER PER PLANTS | 15 | 0.00 |
|  | WEIGHT PER 100 KERNELS(GM) | 15 | 27.34 |
|  | EAR LENGTH(CM) | 15 | 14.80 |
|  | EAR WEIGHT(GM) | 15 | 97.22 |
|  | # OF KERNEL ROWS | 15 | 15.20 |
|  | COB DIAMETER AT MID-POINT(mm) | 15 | 23.39 |
|  | EAR DIAMETER AT MID-POINT(mm) | 15 | 37.05 |
|  | KERNEL LENGTH(MM) | 15 | 10.15 |
|  | KERNEL THICKNESS(mm) | 15 | 5.73 |
|  | KERNEL WIDTH(MM) | 15 | 7.91 |
|  | % ROUND KERNELS(SHAPE GRADE) | 15 | 81.70 |
|  | SHANK LENGTH | 15 | 8.23 |

11. Disease Resistance
LB: Intermediate
NLB: Susceptible
GLS: Intermediate
SLB: Intermediate
CCR(common corn rust): Resistant
GW: Resistant
MDMV Strain A: Resistant
MDMV Strain B: Susceptible 12. Inbred most useful for comparison with the present invention based on genetic makeup and combining ability/maturity characteristics is LH74.

Table 1 indicates that over all environments evaluated the inbred line shows a pollen shed of 7 which is sufficient to allow this line to be used either as a male or as a female though it is preferred as a female.

The purity and homozygosity of inbred ZS0853 is constantly being tracked using isozyme genotypes as shown in Table 2.

TABLE 2

| LINE | ACP1 | ACP4 | ADH | MDH1 | MDH2 | PGD1 | PGD2 | PHI | PGM | IDH2 |
|---|---|---|---|---|---|---|---|---|---|---|
| ZS0853 | 33 | 00 | 22 | 22 | 11 | 11 | 11 | 22 | 22 | 22 |

Isozyme data were generated for Table 2 according to the procedure in Stuber, C. W., Wendell, J. R., Goodman, M. M., And Smith, J. S. C. *Techniques and Scoring Procedures for Starch Gel Electrophoresis of Isozymes from Maize (Zea mays L.).* Tech. Bull. 286. North Carolina Agricultural Research Service, North Carolina State University, Raleigh, N.C., March, 1988.

INDUSTRIAL APPLICABILITY

This invention also is directed to methods for producing a corn plant by crossing a first parent corn plant with a second parent corn plant wherein the first or second parent corn plant is an inbred corn plant from the line ZS0853. Further, both first and second parent corn plants can come from the inbred corn line ZS0853. Thus, any methods using the inbred corn line ZS0853 are part of this invention. The methods include but are not limited to selfing, backcrosses, hybrid production, crosses to populations, and the like. All plants produced using inbred corn line ZS0853 as a parent are within the scope of this invention. Advantageously, the inbred corn line is used in crosses with other, different, corn inbreds to produce first generation ($F_1$) corn hybrid seeds and plants with superior characteristics.

As used herein, the terms "plant and plant parts" include plant cells, plant protoplasts, plant cell tissue culture from which corn plants can be regenerated, plant calli, plant clumps, and plant cells that are intact in plants or parts of plants, such as embryos, pollen, flowers, kernels, ears, cobs, leaves, husks, stalks, roots, root tips, anthers, silk and the like. Corn tissue culture procedures are also described in Green and Rhodes, "Plant Regeneration in Tissue Culture of Maize," Maize for Biological Research (Plant Molecular Biology Association, Charlottesville, Va. 1982, at 36–372). Thus, another aspect of this invention is to provide cells which upon growth and differentiation produce the inbred line ZS0853.

The utility of the dent inbred line ZS0853 extends to the production of plants which may be crosses made with other species. The inbred line may be crossed with sweet corn or popcorn or other dent corn.

Corn is used for human consumption in a variety of different forms, animal consumption, and as a ingredient in many commercial products. The production of corn for human consumption includes products of the dry and wet milling industries. The most commonly recognized uses of corn kernels are corn grits, corn meal, and corn flour. Additional processing can be employed and provide various corn sweeteners and corn starch. Likewise, a variety of snack foods and breakfast foods are made of corn such as corn chips, cornflakes, cornbread, and the like. Likewise, corn oil and various components of corn oil have been used industry and in cooking foods for human consumption.

Additionally corn products can be used to make alcohol products. Alcohol products can be used for human consumption, but likewise, they can be used for industrial purposes. Alcohol products made from corn can be used in gasoline. Flour and starch from corn can be used for sizing, for paper, adhesives, and the like. The corn products have been used in building materials and laundry starches and a variety of other industrial applications. Other parts of the corn plant can also be used. The nongrain portion of the plant and the grain portion of the plant can be chopped and fed to animals. Additionally, corn cobs can be used for firewood and husks can be used for more than just for industrial application they can be used creatively in the arts for the making of corn husk dolls.

The seed, plant and plant parts of the of the inbred corn line ZS0853 and the seed plant and plant parts of the hybrid made with ZS0853 as a parent can be used for various industrial purposes.

EXAMPLES

The following examples compare the traits of the present invention with inbreds and hybrids having similar regions of usage, and/or similar traits and/or characteristics. The data will of course vary depending on the inbred and hybrid employed for the comparison.

Table 3 compares ZS0853 to LH74. Data supplied in this table was generated from means over only those environments where both inbreds were evaluated. LH74 has a (PVP certificate Number 8200063). This is a commercially available inbred. LH74 is an important inbred though declining in use that would be used in similar regions and would cross well with some of the same inbred lines as ZS0853. The data in Table 3 has been collected for a period of 3 years of research testing (when possible).

TABLE 3

PAIRED INBRED COMPARISON DATA

| YEAR | INBRED | VIGOR | EMERGE | PCT TILLER | PLANT HEIGHT | EAR HEIGHT | SHED | EAR QUALITY | PCT BARREN |
|---|---|---|---|---|---|---|---|---|---|
| OVERALL | ZS0853 | 6.1 | 81.5 | 2.0 | 160.6 | 76.0 | 5.4 | 2.8 | |
| | LH74 | 5.8 | 78.6 | 5.4 | 148.2 | 65.7 | 5.2 | 2.6 | |
| | # EXPTS | 30 | 29 | 25 | 30 | 30 | 13 | 20 | |
| | DIFF | 0.2 | 3.0 | 2.8 | 12.4 | 10.3 | 0.2 | 0.2 | |
| | PROB | 0.068*** | 0.083*** | 0.023** | 0.000* | 0.000* | 0.656 | 0.214 | |

| | | HEATP10 | HEATP50 | HEATP90 | HEATS10 | HEATS50 | HEATS90 |
|---|---|---|---|---|---|---|---|
| OVERALL | ZS0853 | 1488 | 1529 | 1589 | 1498 | 1533 | 1570 |
| | LH74 | 1397 | 1436 | 1503 | 1396 | 1431 | 1470 |
| | # EXPTS | 30 | 30 | 30 | 30 | 30 | 30 |
| | DIFF | 91 | 93 | 86 | 102 | 102 | 100 |
| | PROB | 0.000* | 0.000* | 0.000* | 0.000* | 0.000* | 0.000* |

| | | HEATPEEK | HEATBL | BL MOIST | % ROOT LODGE | % STALK LODGE | % DROPPED EARS | MOISTURE | YIELD |
|---|---|---|---|---|---|---|---|---|---|
| OVERALL | ZS0853 | 1439 | 2652 | 25.3 | | | | 10.6 | 52.1 |
| | LH74 | 1336 | 2554 | 28.8 | | | | 10.9 | 53.8 |
| | # EXPTS | 30 | 3 | 3 | | | | 30 | 30 |
| | DIFF | 103 | 98 | 3.5 | | | | 0.3 | 1.7 |
| | PROB | 0.000* | 0.006* | 0.332 | | | | 0.305 | 0.643 |

| | | WARM GERM | COLD GERM | % LRG ROUND | % LRG FLAT | % MED ROUND | % MED FLAT | % SML ROUND | % SML FLAT |
|---|---|---|---|---|---|---|---|---|---|
| OVERALL | ZS0853 | 94.8 | 74.7 | 13.9 | 6.8 | 54.0 | 11.4 | 9.2 | 2.1 |
| | LH74 | 95.5 | 92.0 | 1.5 | 1.8 | 25.3 | 33.8 | 14.4 | 15.8 |
| | # EXPTS | 26 | 26 | 30 | 30 | 30 | 30 | 30 | 30 |
| | DIFF | 0.8 | 17.4 | 12.4 | 5.0 | 28.7 | 22.4 | 5.3 | 13.7 |
| | PROB | 0.423 | 0.000* | 0.000* | 0.000* | 0.000* | 0.000* | 0.003* | 0.000* |

*Probability that a larger difference will occur by chance is ≦0.01.
**Probability that a larger difference will occur by chance is >0.01 and ≦0.05.
***Probability that a larger difference will occur by chance is >0.05 and ≦0.10.

The results of the Table 3 comparison of ZS0853 and LH74 evidence that the inbreds significantly differ in a number of traits. ZS0853 had significantly more seedling vigor 6.1 compared to 5.8 and evidenced significantly better seeding emergence (emerge) than did LH74 (81.5 compared to 78.6 for LH74). LH74 reaches silking and pollination earlier than ZS0853 but black layer moisture statistics are essentially the same with ZS0853 having the lower percentage at 25.3. Additionally seed warm germ percentage is not statistically different for the two lines. ZS0853 averaged 10.6% moisture and a 52.1 bushels to the acre (yield) across locations, which is equivalent to the moisture and yield of LH74.

Table 4 compares ZS0853 crossed to an inbred tester (to form hybrid H1) with LH132 crossed to the same inbred tester (to form hybrid H2). Although hybrid H1 has only recently been placed on sale, both the H1 and the H2 are commercially available hybrids in the same region.

TABLE 4

PAIRED HYBRID COMPARISON DATA

| YEAR | HYBRID | % ROOT LODGE | % STALK LODGE | % DROPPED EARS | TEST WEIGHT | MOISTURE | YIELD | GI |
|---|---|---|---|---|---|---|---|---|
| OVERALL | ZS0853 × INBRED TESTER | 0.6 | 3.4 | 0.4 | 49.3 | 24.4 | 130.7 | 160.6 |
| | LH132 × INBRED TESTER | 0.9 | 1.9 | 0.2 | 49.3 | 27.7 | 129.6 | 161.8 |
| | # EXPTS | 220 | 220 | 220 | 36 | 220 | 220 | 220 |
| | DIFF | 0.3 | 1.5 | 0.2 | 0.0 | 3.3 | 1.1 | 1.1 |
| | PROB | 0.017** | 0.000* | 0.005* | 0.976 | 0.000* | 0.258 | 0.084*** |

TABLE 4-continued

PAIRED HYBRID COMPARISON DATA

| YEAR | INBRED | PLANT HEIGHT | EAR HEIGHT | 50% POLLEN | MATURITY |
|---|---|---|---|---|---|
| OVERALL | ZS0853 × INBRED TESTER | 233 | 101 | 1327 | 108 |
| | LH132 × INBRED TESTER | 223 | 93.1 | 1320 | 114 |
| | # EXPTS | 16 | 16 | 18 | 220 |
| | DIFF | 9.9 | 8.1 | 7 | 6 |
| | PROB | 0.003* | 0.024** | 0.365 | |

*Probability that a larger difference will occur by change is ≦0.01.
**Probability that a larger difference will occur by change is >0.01 and ≦0.05.
***Probability that a larger difference will occur by change is >0.05 and ≦0.10.

The results of Tables 4 comparing ZS0853 in hybrid combination show that compared to H2 inbred ZS0853 in hybrid combination has significantly less root lodging (0.6 vs. 0.9) than H2 though more stalk lodging and dropped ears. Both hybrids have similar ratings on the other evaluated characteristics except ear height and moisture. The two inbred lines differ significantly in moisture. ZS0853 has a moisture percentage of 24.4 compared to 27.7 for LH74. The moisture percentage is important because at time of grain sale the moisture is assessed and if the moisture is too high the grain will have to go through a costly drying process. The higher the percentage of moisture the more drying time (and cost) will be required to each acceptable levels. Thus the moisture percentage in a hybrid at harvest is an important factor. The yield (130.7 bushel per acre) for H1 compared to H2 yield (129.6 bushels per acre) were essentially equivalent.

Table 5 show the yield and moisture comparisons between a hybrid containing ZS0853 and other commercial hybrids on the market. A positive ADV equals a positive advantage for the ZS0853 hybrid compared with the commercial hybrid.

| HYBRID | YLD | ADV | MOIST | ADV |
|---|---|---|---|---|
| ZS0853 | 121.9 | 4.0 | 22.2 | 0.8 |
| 3563 | 117.9 | | 23.0 | |
| ZS0853 | 153.8 | 5.3 | 16.6 | 2.0* |
| 3475 | 148.5 | | 18.6 | |
| ZS0853 | 141.8 | 8.8* | 16.4 | 3.9* |
| 3417 | 132.9 | | 20.3 | |

*.10 level significance.

Clearly Table 5 evidences ZS0853 has excellent yielding potential in hybrid combination. ZS0853 has better moisture levels and better yield levels than most of the above listed commercial hybrids.

The ZS0853 hybrid would be utilized in generally the same region of the corn belt in which LH74 flourishes. A comparison shows that inbred ZS0853 provides significant advantage for seedling vigor, emergence of corn seedlings, and fewer tillers. Low numbers of tillers are desirable because $F_1$ hybrid seed is frequently developed by detasselling the female corn plant and allowing the male corn plant to tassel and pollinated the female. Tillers on females can generate tassels after detasselling is completed. These tassels can than contaminate the $F_1$ seed production. Therefore if using an inbred as a female low tiller numbers is an advantage. Additionally ZS0853 produces a large percentage of medium round kernels, significantly more than does LH74. Uniformity in kernel shape and size may cause less planter problems at spring planting time. ZS0853 has silking and pollination characteristics which make the inbred sufficiently flexible to be used as a male or female when producing hybrid seed. Additionally the inbred has excellent yield and moisture results in hybrid combination.

Inbred seeds of ZS0853 have been placed on deposit at the American Type Culture Collection (ATCC), Rockville, Md. 20852, under deposit accession number 75688. This inbred corn line seed has been deposited under the Budapest Treaty and under that treaty it is understood that ZS0853 will be maintained without restriction. It is also understood that the released of the seed does not give any party the right to infringe the patent claims.

Although the invention has been described with respect to a preferred embodiment thereof, it is to be also understood that it is not to be so limited since changes and modifications can be made therein which are within the full intended scope of this invention as defined by the appended claims.

What is claimed is:

1. An inbred corn line designated ZS0853, seed of which have been deposited under ATCC Accession No. 75688.

2. Pollen of the plant of claim 1.

3. Seed or Seeds of the inbred corn line designated ZS0853 of claim 1.

4. An inbred corn plant with all the phenotypic, physiological and morphologic characteristics of inbred corn line of claim 1.

5. A method for producing a corn plant, comprising the steps of:

(a) crossing a first parent corn plant with a second parent corn plant wherein said first or second parent corn plant is the inbred corn plant ZS0853, wherein ZS0853 has resistance to rust, low moisture potential in hybrid combination, and has been deposited under ATCC Accession No. 75688; and, (b) harvesting and growing the seed produced from said cross.

6. The method of claim 5, wherein said first and second parent corn plants are both from the inbred corn line designated ZS0853.

7. The method of claim 5, wherein said first or second parent corn plant having the designation ZS0853 is the female parent.

8. The method of claim 5, wherein said first or second parent corn plant having the designation ZS0853 is the male parent.

9. A method for producing first generation ($F_1$) hybrid corn seed characterized by the low moisture at harvest shown by inbred ZS0853, seed of which have been deposited under ATCC Accession No. 75688, comprising crossing a first inbred parent corn plant with a second inbred parent corn plant, wherein said first or second parent corn plant is the inbred corn plant having the designation ZS0853 and evidencing the ZS0853 trait of low moisture at harvest, and harvesting the seed produced from said cross.

10. A first generation ($F_1$) hybrid corn plant having seed characterized by low moisture at harvest shown by inbred ZS0853 said hybrid corn plant produced by growing said hybrid corn seed of claim 9.

11. A tissue culture comprising regenerable cells of the inbred corn plant of claim 1.

* * * * *